US009295846B2

(12) United States Patent
Westlund et al.

(10) Patent No.: US 9,295,846 B2
(45) Date of Patent: Mar. 29, 2016

(54) MUSCLE AND NERVE STIMULATION (71) Applicant: Respicardia, Inc., Minnetonka, MN (US)

(72) Inventors: Randy W. Westlund, River Falls, WI (US); Kristofer J. James, Eagan, MN (US); Mark Gelfand, New York, NY (US)

(73) Assignee: Respicardia, Inc., Minnetonka, MN (US)

( * ) Notice: Subject to any disclaimer, the term of this patent is extended or adjusted under 35 U.S.C. 154(b) by 0 days.

(21) Appl. No.: 13/851,243

(22) Filed: Mar. 27, 2013

(65) Prior Publication Data

US 2014/0114371 A1    Apr. 24, 2014

Related U.S. Application Data (63) Continuation of application No. 12/367,024, filed on Feb. 6, 2009, now Pat. No. 8,433,412.

(60) Provisional application No. 61/063,960, filed on Feb. 7, 2008.

(51) Int. Cl.
| *A61N 1/00* | (2006.01) |
| *A61N 1/365* | (2006.01) |
| *A61N 1/39* | (2006.01) |
| *A61N 1/36* | (2006.01) |
| *A61N 1/37* | (2006.01) |
| *A61N 1/05* | (2006.01) |

(52) U.S. Cl.
CPC .............. *A61N 1/36542* (2013.01); *A61N 1/05* (2013.01); *A61N 1/056* (2013.01); *A61N 1/3611* (2013.01); *A61N 1/36139* (2013.01); *A61N 1/36521* (2013.01); *A61N 1/37* (2013.01); *A61N 1/3962* (2013.01); *A61N 1/0551* (2013.01); *A61N 1/0558* (2013.01); *A61N 2001/0585* (2013.01)

(58) Field of Classification Search
CPC ....... A61N 1/05; A61N 1/0551; A61N 1/056; A61N 1/3611; A61N 1/36139; A61N 1/36521; A61N 1/36542; A61N 1/37; A61N 1/3962; A61N 2001/0585; A61N 1/0558
See application file for complete search history.

(56) References Cited

U.S. PATENT DOCUMENTS

| 4,129,125 A | 12/1978 | Lester et al. |
| 4,702,253 A | 10/1987 | Nappholz et al. |
| 4,827,935 A | 5/1989 | Geddes et al. |
| 4,830,008 A | 5/1989 | Meer |
| 5,002,067 A | 3/1991 | Berthelsen et al. |

(Continued)

FOREIGN PATENT DOCUMENTS

| DE | 10103288 A1 | 8/2002 |
| WO | 2008092246 A1 | 8/2008 |

OTHER PUBLICATIONS

Thoma, H. et al., The Vienna Phrenic Pacemaker, Longterm Data of Failures.

(Continued)

*Primary Examiner* — George Manuel
(74) *Attorney, Agent, or Firm* — Frank P. Piskolich (57) ABSTRACT

A lead system for an implantable medical device and applications for the lead system. Also includes therapeutic systems, devices, and processes for detecting and treating disordered breathing and treating cardiac and breathing issues together with an implantable device.

17 Claims, 10 Drawing Sheets

(56) References Cited

U.S. PATENT DOCUMENTS

| | | | |
|---|---|---|---|
| 5,056,519 A | 10/1991 | Vince | |
| 5,146,918 A | 9/1992 | Kallok et al. | |
| 5,170,802 A | 12/1992 | Mehra | |
| 5,199,428 A | 4/1993 | Obel et al. | |
| 5,265,604 A | 11/1993 | Vince | |
| 5,330,507 A | 7/1994 | Schwartz | |
| 5,423,865 A | 6/1995 | Bowald et al. | |
| 5,483,969 A | 1/1996 | Testerman et al. | |
| 5,485,851 A | 1/1996 | Erickson | |
| 5,524,632 A | 6/1996 | Stein et al. | |
| 5,578,061 A | 11/1996 | Stroetmann et al. | |
| 5,800,470 A | 9/1998 | Stein et al. | |
| 5,922,014 A | 7/1999 | Warman et al. | |
| 5,938,694 A | 8/1999 | Jaraczewski et al. | |
| 6,006,134 A * | 12/1999 | Hill et al. | 607/9 |
| 6,132,384 A | 10/2000 | Christopherson et al. | |
| 6,212,435 B1 | 4/2001 | Lattner et al. | |
| 6,266,564 B1 | 7/2001 | Hill et al. | |
| 6,314,324 B1 | 11/2001 | Lattner et al. | |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,641,542 B2 | 11/2003 | Cho et al. | |
| 6,684,101 B2 | 1/2004 | Daum et al. | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 | 7/2006 | Park et al. | |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al | |
| 7,223,244 B1 | 5/2007 | Koh et al. | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 | 3/2008 | Falkenberg et al. | |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 7,813,805 B1 | 10/2010 | Farazi | |
| 2001/0003799 A1 | 6/2001 | Boveja | |
| 2002/0049479 A1 | 4/2002 | Pitts | |
| 2002/0128563 A1 | 9/2002 | Carlson et al. | |
| 2003/0078623 A1 | 4/2003 | Weinberg et al. | |
| 2003/0088244 A1 | 5/2003 | Swanson et al. | |
| 2003/0195571 A1 | 10/2003 | Burnes et al. | |
| 2005/0043765 A1 | 2/2005 | Williams et al. | |
| 2005/0085734 A1 | 4/2005 | Tehrani et al. | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0165457 A1 | 7/2005 | Benser et al. | |
| 2005/0197588 A1 | 9/2005 | Freeberg | |
| 2005/0240240 A1 | 10/2005 | Park et al. | |
| 2005/0288729 A1 | 12/2005 | Libbus et al. | |
| 2006/0030894 A1 | 2/2006 | Tehrani | |
| 2006/0036294 A1 | 2/2006 | Tehrani | |
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0184060 A1 | 8/2006 | Belalcazar et al. | |
| 2006/0229677 A1 | 10/2006 | Moffitt et al. | |
| 2006/0247729 A1 | 11/2006 | Tehrani et al. | |
| 2007/0021795 A1 | 1/2007 | Tehrani | |
| 2007/0118183 A1 | 5/2007 | Gelfand et al. | |
| 2007/0156199 A1 | 7/2007 | Koh et al. | |
| 2007/0260285 A1 | 11/2007 | Libbus et al. | |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0183254 A1 | 7/2008 | Bly et al. | |
| 2008/0183259 A1 | 7/2008 | Bly et al. | |
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |
| 2008/0234694 A1 | 9/2008 | Stegfeldt et al. | |
| 2009/0088827 A1 | 4/2009 | Tockman et al. | |
| 2010/0249630 A1 | 9/2010 | Droitcour et al. | |
| 2011/0060380 A1 | 3/2011 | Gelfand et al. | |

OTHER PUBLICATIONS

Redline, Susan et al., Beyond the Fat Boy, Journal of Applied Physiology 2005, vol. 99: pp. 1243-1244.

Ester, Murray et al., Is Obstructive Sleep Apnea the Cause of Sympathetic Nervous Activation in Human Obesity?, Journal of Applied Physiology 2006, vol. 100, pp. 11-12.

Caples, Sean M. et al., Influence of Cardiac Function and Failure on Sleep-Disordered Breathing, Journal of Applied Physiology 2005, vol. 99, pp. 2433-2439.

Punjabi, Naresh M. et al., Disorders of Glucose Metabolism in Sleep Apnea, Journal of Applied Physiology 2005, vol. 99, pp. 1998-2007.

Leuenberger, Urs A. et al., Hypoxia Augments Apnea-Induced Peripheral Vasoconstriction in Humans, Journal of Applied Physiology 2001, vol. 90, pp. 1516-1522.

Ishii, Kiyoshi, Effects of Bilateral transvenous diaphrahm pacing on hemodynamic function in patients after cardiac operations, 1990.

Parati, Gianfranco et al., Sleep Apnea: Epidemiology, Pathophysiology, and Relation to Cardiovascular Risk, Am Journal Physiological Society 2007, vol. 293, pp. R1671-R1683.

Gottfried, Stewart B. et al., Effects of Phrenic Stimulation on Upper Airway Resistance in Anesthetized Dogs, Am Physiological Society 1983, 0161-7567/83 pp. 419-426.

Planas, Roque F. et al., Diaphragmatic Pressures: Transvenous vs. Direct Phrenic Nerve Stimulation, Am Physiological Society 1985, 0161-7567/85, pp. 269-273.

Series, F. et al., Site of Phrenic Nerve Stimulation-Induced Upper Airway Collapse: Influence of Expiratory Time, Journal of Applied Physiology 2002, vol. 92, pp. 665-671.

Kingma, John G. Jr. et al., Neuromodulation Therapy Does Not Influence Blood Flow Distribution or Lef-Ventricular Dynamics During Acute Myocardial Ischemia, Autonomic Neuroscience; Basic and Clinical 91 (2001) pp. 47-54.

Linderroth, Bengt, MD, PHD et al., Mechanisms of Spinal cord Stimulation in Painful Syndromes: Role of Animals Models, American Academy of Pain Medicine, vol. 7, No. S14-S26, 2006.

Tanaka, Satoshi et al., Mechanisms of Sustained Cutaneous Vasodilation Induced by Spinal Cord Stimulation, Autonomic Neuroscience: Basic and Clinical 114 (2004) pp. 55-60.

Orenzi-Filho, Geraldo et al., Cheyne-Stokes Respiration in Patients with Congestive Heart Failure: Causes and Consequences, Clinics 2005; 60 (4): 333-44.

(56) References Cited

OTHER PUBLICATIONS

Brack, Thomas, Cheyne-Stokes Respiration in Patients with Congestive Heart Failure, Seiss Med Wkly 2003; 133:605-610, www.smw.ch.

Yumino, Dai et al., Central Sleep Apnea and Cheyne-Stokes Respiration, Proceedings of the American Thoracic Society, 2008, vol. 5, pp. 226-236.

Garrido-Garcia, H. et al., Treatment of Chronic Ventilatory Failure Using a Diaphragmatic Pacemaker, Spinal Cord (1998) 36, 310-314.

Diedrichs, Holger et al., Symptomatic Relief Prececes Improvement of Myocardial Blood Flow in Patients Under Spinal cord Stimulation, BioMed Central, 2005, pp. 1-7.

Kaneko, S. et al., A New Approach to Respiratory Assist for Phrenic Nerve Paralysis, Trans Am Soc. Artif Intern Organs, 1985, vol. XXXI, pp. 301-304.

Macintyre, Neil R., MD, Setting the Frequency-Tidal Volume Pattern, www.rcjournal.com/contents/03.02/03.02.0266.asp.

Kohnlein, T. et al., Central Sleep Apnea Syndrome in Patients with Chronic Heart Disease: A Critical Review of the Current Literature, Thoarx 2002; 57:547-554.

Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.

Dobelle, William H., Use of Breathing Pacemakers to Suppress Intractable Hiccups of up to Thirteen Years Duration, ASAIO Journal 1999, pp. 524-252.

Series, Frederic, Assessment of Upper Airway Dynamics in Awake Patients with Sleep Apnea Using Phrenic of Nerve Stimulation, Am Journal Respir Crit Care Med, 2000, vol. 162., pp. 795-800.

Bilgutay, A.M. et al., Augmented Ventilation by Synchronous Phrenic Nerve Stimulation, Trans. Amer. Soc. Artif. Int. Organs, 1970, vol. XVI, pp. 213-217.

Yasuma, Fumihiko et al., Eight-Year Follow-Up Study of a Patient with Central Alveolar Hypoventilation Treated with Diaphragm Pacing, Respiration, 1998: 65:313-316.

Handa, Y. et al., Basic Studies on Electrophrenic Respiration Pat 2-Assisted Ventilation by the Synchronous Electrophrenic Respirator, Medical and Biological Engineering, Jul. 1976.

Kimura, M. et al., Heart Rate and BodyTemperature Sensitive Diaphragm Pacing, Med. & Biol. Eng. & Comput. 1992, 30, 155-161.

Kimura, M. et al., A Heart-Rate-Responsive Diaphragm Pacemaker, Med. & Biol. Eng. & Comput., 1987, 25, 458-462.

Kimura, M. et al., Addition to an RF-Couples Phrenic Nerve Stimulator Implant to Provide Outward Transmission of Body Temperature, Med. & Biol. Eng. & Comput. 1986, 24, 659-661.

Taira, Takaomi, MD, PHD et al., Phrenic Nerve Stimulation for Diaphragm Pacing with a Spinal Cord Stimulator, Elsevier Science, Surg Neural, 2003; 59:128-32.

Chatfield, Paul O. et al., Role of Pulmonary Proprioceptive Reflexes in Suppression of Spontaneous Breating During Electrophrenic Respiration, Dept. of Physiology, Harvard Medical School, and Dept. of Phsiology, Harvard School of Public Health, vol. 163.

Sarnoff, Stanley J. et al., Electrophrenic Respiration, III. Mechanism of the Inhibition of Spontaneous Respiration, Dept. of Physiology, Harvard School of Public Health, 1948, vol. 155, pp. 203-207.

Sarnoff, Stanley J. et al, Electrophrenic Respiration IV, The Effectivenessof Contralateral Ventilation During Activity of One Phrenic Nerve, Dept. of Physiology, Harvard School of Public Health, 1949, pp. 929-937.

Stemmer, Edward A. MD et al., Diaphragmatic Pacing in the Treatment of Hypoventilation Syndrome, Journal of Thoracic and Cardiovascular Surgery, vol. 54, No. 5, 1967, pp. 649-657.

Furman, Seymour, MD et al., Transvenous Stimulation of the Phrenic Nerves, Journal of Thoracic and Cariovascular Surgery, vol. 62, No. 5, 1971, pp. 743-751.

Aiyar, Harish et al., Diaphragm Pacing for Chronic Respiratory Insufficiency, CRC Press, LLC, 2001, Chapter 9.

Oliven, Arie et al., Upper Airway Response to Electrical Stimulation of the Genioglossus in Obstructive Sleep Apnea, Journal of Applied Physiology, 95:2023-2029, 2003.

Javaheri, Shahrokh, MD, Acetazolamide Improves Central Sleep Apnea in Heart Failure Pulmonary Service, Department of Veterans Affairs Medical Center, and Department of Medicine, University of Cincinnati College of Medicine, Cincinnati, Ohio Am J Respir Crit Care Med vol. 173, pp. 234-237, 2006, Jul. 5, 2005.

Vaseghi, et al., Behond Coronary Sinus Angiography: The Value of Coronary Arteriography and Identification of the Pericardiophrenic Vein During Left Ventricular Lead Placement, PACE, 2005, vol. 28.

Leung, Richard S. T. et al., Influence of Cheyne-Stokes Respiration on Cardiovascular Oscillations in Heart Failure, Am J Respir Cri Care Med, 2003, vol. 167. pp. 1534-1539.

Esther, Doris J. W., Clinical Control of Respiration by Tranvenous Phrenic Pacing, Trans. Amer. Soc. Artif. Int. Organs., vol. XIV, 1968.

Levy, T. et al., A Comparison Between Passive and Active Fixation Leads in the Coronary Sinus for biatrial Pacing, The European Society of Cardiology 2000.

Javaheri, Shahrokh M.D., CPAP Should Not Be Used for Central Sleep Apnea in Congestive Heart Failure Patients, Journal of Clinical Sleep Medicine, vol. 2, No. 4, 2006.

Hall, Michael J. et al., Cycle Length of Periodic Breathing in Patients with and without Heart Failure, Am. J. Respir. Crit. Care Med vol. 154, pp. 376-381, 1996.

Hasdemir, Can MD et al., Jpn Heart J, vol. 44 No. 3, 2003.

Schauerte, Patrick et al., Catheter Stimulation of Cardiac Parasympathetic Nerves in Humans: A Novel Approach to the Cardiac Autonomic Nervous System, American Heart Association 2006.

Shaul, Donald B., et al., Thoracoscopic Placement of Phrenic Nerve Electrodes for Diaphragmatic Pacing in Children, Journal of Pediatric Surgery, vol. 37, No. 7 pp. 974-978, 2002.

Plisiene, Jurgita et al., Selective Transvascular Stimulation of Cariac Autonomic Nerves: A Novel Technique, Biomedicine vol. 2 No. 1, Jul. 2002.

Arzt, Michael et al., Treatment of Sleep Apnea in Heart Failure, Am J Respir Crit Care Med vol. 173, pp. 1300-1308, 2006.

* cited by examiner

MUSCLE AND NERVE STIMULATION

CROSS REFERENCE TO RELATED APPLICATIONS

This application is a continuation of U.S. patent application Ser. No. 12/367,024 filed Feb. 6, 2009, entitled "Muscle and Nerve Stimulation," and claims priority of U.S. Provisional Application 61/063,960, filed Feb. 7, 2008, entitled Muscle and Nerve Stimulation System. The disclosures of these applications are incorporated by reference.

BACKGROUND

Many people with cardiac disorders are also afflicted with pulmonary conditions. In some cases progression of a cardiac condition or respiratory condition can be monitored and understood by measuring changes over time of the functioning of the concomitant system. As one example, central sleep apnea may occur in heart failure patients that can benefit from a cardiac device.

SUMMARY

Embodiments of the present invention relate generally to a lead-electrode system for use with an Implantable Medical Device (IMD) configured to monitor and/or treat both cardiac and respiratory conditions. More particularly, embodiments of the invention relate to a lead-electrode configuration of a combination IMD that combines therapies such as cardiac pacing, respiratory sensing, phrenic nerve stimulation, defibrillation, and/or biventricular pacing, referred to herein as cardiac resynchronization therapy ("CRT").

IMDs that incorporate cardiac pacing, defibrillation (ICD), and a feedback loop for sensing ECG and respiration signals, may also perform monopolar or bipolar phrenic nerve stimulation. Monopolar stimulation devices typically employ an implantable pulse generator, a single lead having one or more active electrodes, and a separate indifferent electrode. The active electrodes serve as the negative pole, and are normally disposed near the phrenic nerve stimulation lead distal end. An indifferent electrode is frequently located on the exterior of the IMD housing, which functions as the anode or positive pole. Electrical stimulation occurs as impulses of current flow between the active electrode and the indifferent electrode through the body tissue. Monopolar stimulation produces a radial current diffusion that covers an approximately spherical space around the active electrode and can stimulate a nearby phrenic nerve.

In contrast to monopolar stimulation systems, bipolar stimulation systems utilize one or more electrodes on the lead as the positive pole, and one or more of the remaining electrodes on the lead acts as the negative pole. The IMD housing is not used as an indifferent electrode. Usually, two adjacent or nearby electrodes are activated and respectively function as positive and negative poles. Bipolar stimulation creates a narrower and more focused current field than monopolar stimulation. However, monopolar stimulation is frequently used because it and be simpler to implement and it enables construction of simpler, smaller caliber electrode leads for transvenous placement in small caliber veins. This issue may be valuable if electrodes are inserted into veins that are 1.5 to 3.5 mm in diameter such as pericardiophrenic veins, although inventors have successfully employed bipolar leads in pericardiophrenic veins to stimulate the phrenic nerve.

In accordance with embodiments of the present invention, phrenic nerve stimulation may be bipolar or monopolar. Stimulation and/or sensing leads may be placed in a small pericardiophrenic vein, a brachiocephalic vein, an azygos vein, a thoracic intercostal vein, or other thoracic vein that affords proximity to the phrenic nerve for stimulation. Alternatively or in combination, an existing cardiac lead (i.e. pacing or shocking lead residing in the superior vena cava, right atrium, right ventricle, coronary vein adjacent the left ventricle, or other cardiac structure) may also be used for phrenic nerve pacing. Steroid eluting features may be provided on the lead system to reduce inflammation associated with the placement of the leads. Respiratory sensing may be obtained via transthoracic impedance. It should also be appreciated that the IMD may be placed on the right and/or left side of the patient's body.

In one embodiment in accordance with the invention, a lead system for an implantable medical device includes an intravascularly implantable cardiac lead usable for stimulating cardiac tissue and an intravascularly implantable respiration lead for transvascularly stimulating a phrenic nerve. Embodiments of the cardiac lead include, but are not limited to, pacemaker leads, defibrillation leads, and/or CRT leads. Embodiments of the respiration lead may be installed in a pericardiophrenic vein, a brachiocephalic vein, an internal jugular vein, a superior intercostal vein, the superior vena cava, or other appropriate locations. Embodiments of the respiration lead may include pre-formed biases that assist in stabilizing the lead in the vein and positioning electrodes on the lead proximate a phrenic nerve.

In another embodiment in accordance with the invention, a method of treating an irregular heart rhythm with an implantable medical device includes detecting signals representative of respiration and applying a defibrillation pulse when the respiration signal indicates that the lungs are in a low impedance state.

In yet another embodiment in accordance with the invention, a method of treating an irregular heart rhythm includes stimulating a phrenic nerve to cause respiration to occur at a level greater than metabolic demand and applying a defibrillation pulse during a period of reduced breathing caused by the phrenic nerve stimulation.

Another embodiment in accordance with the invention involves a method of calibrating an implantable medical device that includes stimulating a phrenic nerve to cause respiration to occur at a level greater than metabolic demand and calibrating the cardiac related circuitry of the device during a period of reduced breathing caused by the phrenic nerve stimulation.

An embodiment in accordance with the invention includes a respiration sensing system for use with an implantable medical device having an intravascular azygos lead with at least one electrode configured to be located in the azygos vein, an implantable medical device with at least one electrode configured to be implanted subcutaneously in a patient's chest, and circuitry within the implantable medical device that measures impedance between the at least one electrode on the azygos lead and the at least one electrode on the implantable medical device. In an optional variation of this embodiment, the azygos lead further includes at least one stimulation electrode that is configured to be positioned proximate a phrenic nerve.

In another embodiment in accordance with the invention, a respiration sensing system for use with an implantable medical device has an intravascular azygos lead with at least one electrode configured to be located in the azygos vein, an implantable medical device with at least one electrode configured to be implanted subcutaneously in a patient's chest, and circuitry within the implantable medical device that measures impedance between the at least one electrode on the azygos lead and the at least one electrode on the implantable medical device. In this embodiment an electrode on the azygos lead is located proximate the diaphragm and the circuitry samples impedance measurements between the at least one electrode on the azygos lead and the at least one electrode on the implantable medical device at an interval and samples diaphragmatic EMG at an electrode proximate the diaphragm at an interval so that samples of impedance and EMG can be taken at separate times.

In yet another embodiment, a respiration sensing system for use with an implantable medical device has an intravascular azygos lead with at least one electrode configured to be located in the azygos vein, an implantable medical device with at least one electrode configured to be implanted subcutaneously in a patient's chest, and circuitry within the implantable medical device that measures impedance between the at least one electrode on the azygos lead and the at least one electrode on the implantable medical device. In this embodiment an electrode on the azygos lead is located proximate the diaphragm and the circuitry samples impedance measurements between the at least one electrode on the azygos lead and the at least one electrode on the implantable medical device at an interval and samples electrocardiogram measurements between the at least one electrode on the azygos lead and the at least one electrode on the implantable medical device at an interval so that samples of impedance and electrocardiogram measurements can be taken at separate times Another embodiment includes a respiration sensing system for use with an implantable medical device having an intravascular azygos lead with at least one electrode configured to be located in the azygos vein, an implantable medical device with at least one electrode configured to be implanted subcutaneously in a patient's chest, and circuitry within the implantable medical device that measures impedance between the at least one electrode on the azygos lead and the at least one electrode on the implantable medical device. In this embodiment an electrode on the azygos lead is located proximate the diaphragm and the circuitry samples impedance measurements between the at least one electrode on the azygos lead and the at least one electrode on the implantable medical device at an interval and samples diaphragmatic EMG at an electrode proximate the diaphragm at an interval and samples electrocardiogram measurements between the at least one electrode on the azygos lead and the at least one electrode on the implantable medical device at an interval so that samples of each of the three measurements can be taken at separate times.

In another embodiment in accordance with the invention, a sensing system includes an intravascular azygos lead with at least two electrodes configured to be located in the azygos vein proximate the diaphragm and circuitry that samples measurements of diaphragmatic EMG based on signals received by the at least two electrodes. In an optional variation of this embodiment, the azygos lead further includes at least one stimulation electrode that is configured to be positioned proximate a phrenic nerve.

In yet another embodiment in accordance with the invention, a sensing system includes an intravascular azygos lead with at least two electrodes configured to be located in the azygos vein proximate the diaphragm and circuitry that samples measurements of diaphragmatic EMG based on signals received by the at least two electrodes. This embodiment includes an implantable medical device having at least one electrode configured to be implanted subcutaneously in a patient's chest and circuitry that samples electrocardiogram measurements between at least one electrode on the azygos lead and the at least one electrode on the implantable medical device at an interval so that samples of diaphragmatic EMG and electrocardiogram signals can be taken at separate times.

DETAILED DESCRIPTION

In FIGS. 1-8, heart anatomy is labeled consistently: Right Atrium 10, Left Atrium 12, Left Ventricle 14, and Right Ventricle 16. Veins and nerves are also labeled consistently: Azygos Vein 18, Right Pericardiophrenic Vein 20, Right Phrenic Nerve 22, Right Brachiocephalic Vein 24, Left Brachiocephalic Vein 26, Left Vagus Nerve 28, Left Phrenic Nerve 30, Left Pericardiophrenic Vein 32, Superior Vena Cava 34, Left Superior Intercostal Vein 37, Left Internal Jugular Vein 38, and Right Internal Jugular Vein 39.

Figure 1:
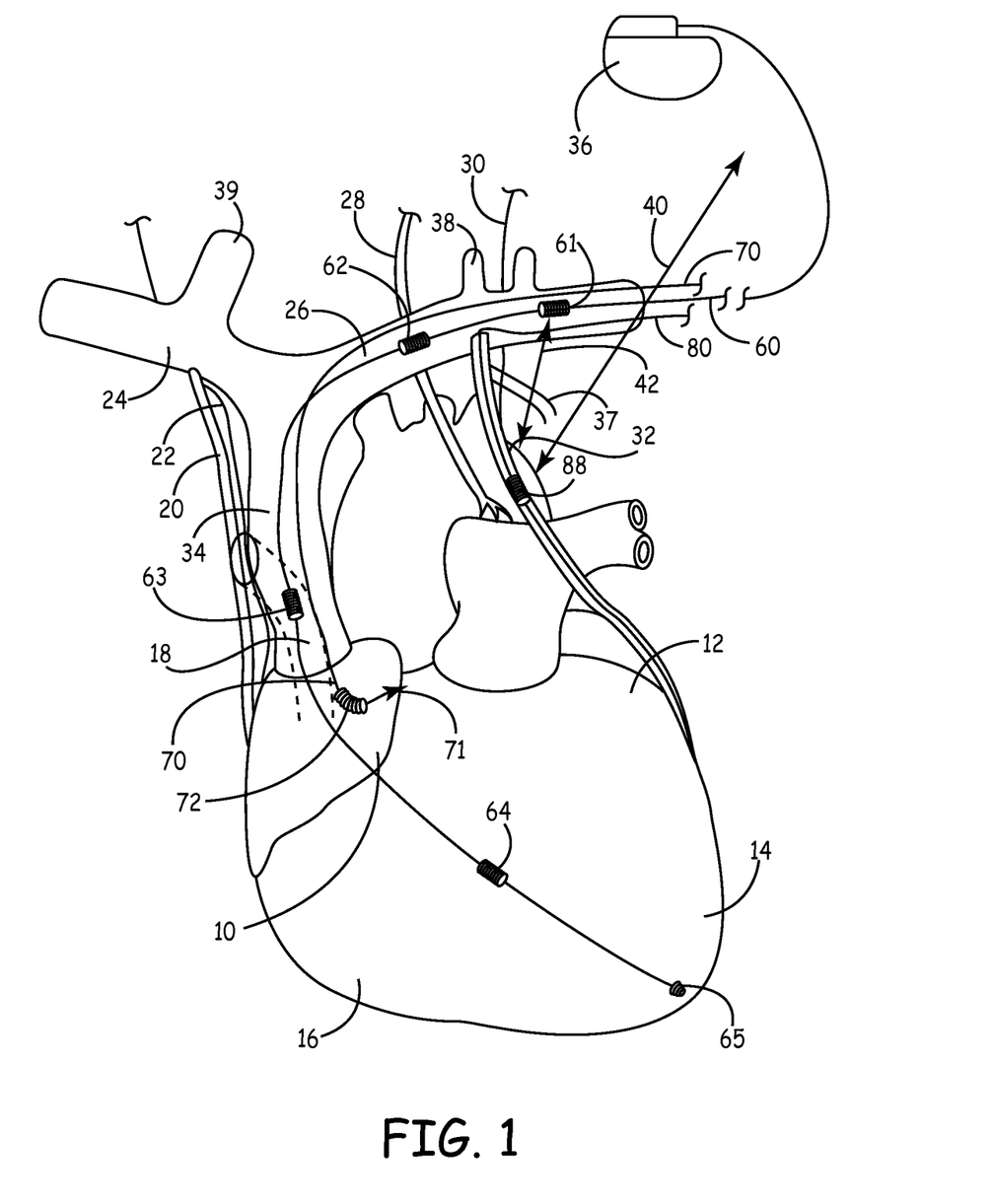
FIG. 1 is a schematic view of a device and lead system in accordance with embodiments of the invention.

FIG. 1 is a schematic view of a device and lead system in accordance with embodiments of the invention. FIG. 1 depicts an embodiment where the IMD 36 is implanted in the left chest. Right ventricular lead 60 has electrodes 61, 62, 63, 64, and 65 for stimulation and/or sensing purposes, where 61 and 62 are situated on the lead 60 to be positioned medial and/or lateral to the ostium of pericardiophrenic vein 32 for phrenic nerve stimulation. Right atrial lead 70 has electrodes 71 and 72 for stimulation and/or sensing purposes. Left phrenic nerve 30 stimulation is obtained by a monopolar active electrode 88 on left phrenic lead 80 in the left pericardiophrenic vein 32 and an indifferent stimulation electrode comprised of the IMD 36 housing. The stimulation electrode 88 may also be used for sensing as indicated by stimulation and/or sensing vector 40. Alternatively, an extended bipolar configuration comprised of electrode 88 and any electrode of right ventricular lead 60, most preferably electrode 61, is utilized. This configuration 30 defines stimulation and/or sensing vector 42. In any of the embodiments described in FIGS. 1-8 or elsewhere herein, a left ventricular stimulation lead (not shown) may be fed through a coronary vein or otherwise situated to stimulate the left ventricle in patients requiring CRT.

Figure 2:
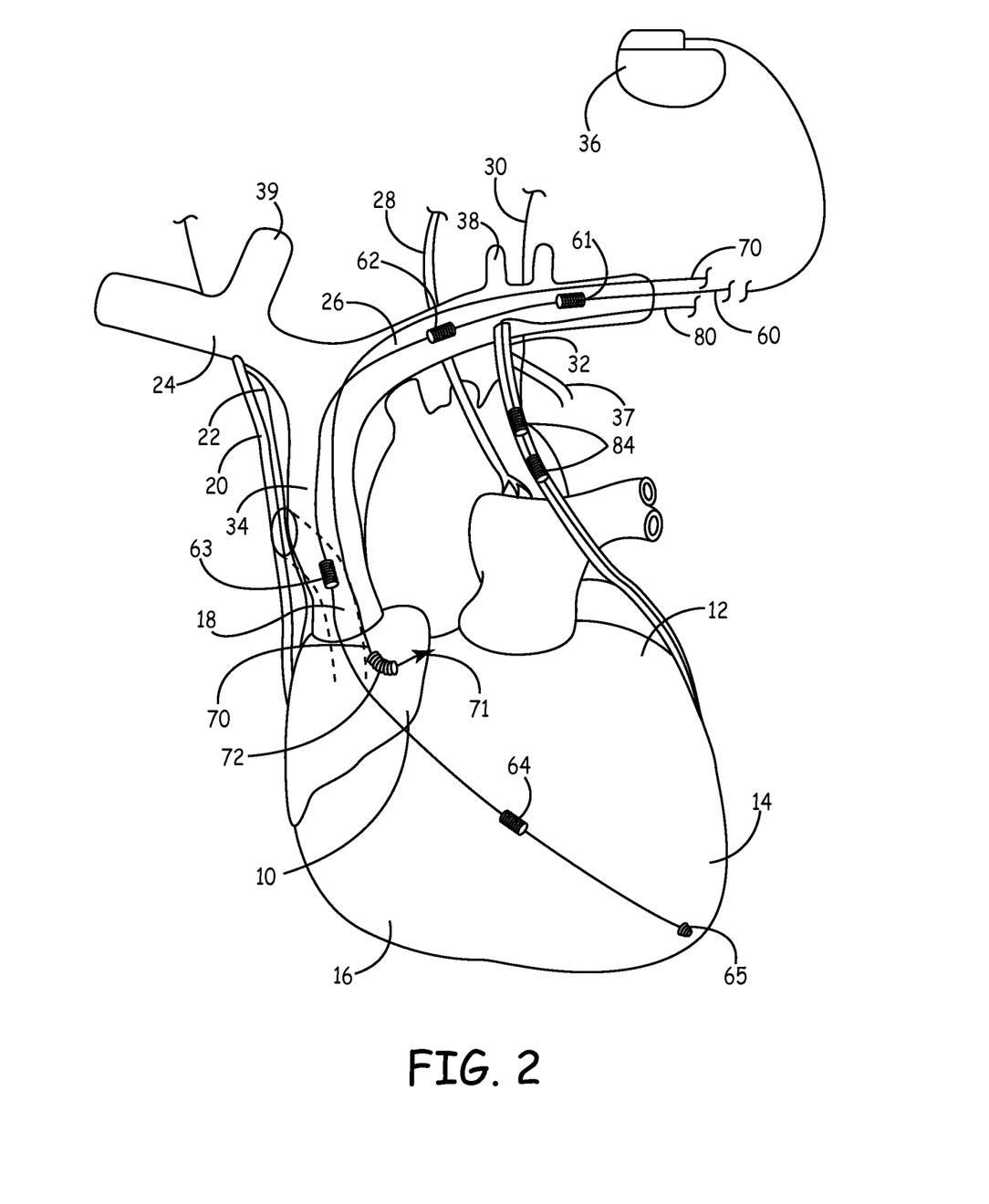
FIG. 2 is a schematic view of a device and lead system in accordance with embodiments of the invention.

FIG. 2 is a schematic view of a device and lead system in accordance with embodiments of the invention. FIG. 2 depicts another embodiment where the IMD 36 is implanted in the left chest. Left phrenic nerve 30 stimulation is obtained by bipolar electrodes 84 on left phrenic lead 80 in the left pericardiophrenic vein 32. One or more of the bipolar electrodes 84 or cardiac pacing electrodes on right atrial lead 70 or right ventricular lead 60 may be used for sensing respiration with IMD 36 housing serving as a reference sensing electrode as is well known in the art.

Figure 3:
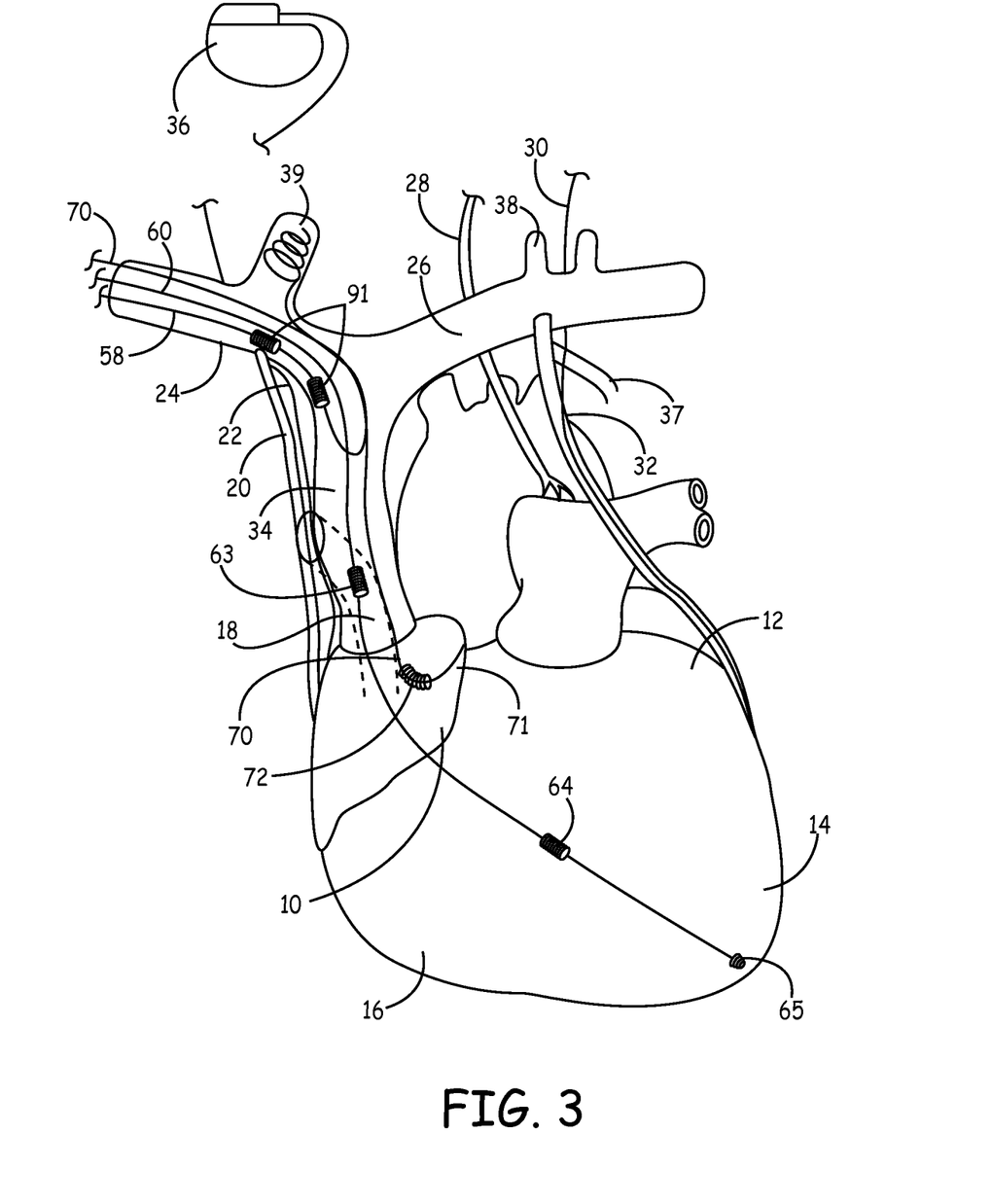
FIG. 3 is a schematic view of a device and lead system in accordance with embodiments of the invention.

FIG. 3 is a schematic view of a device and lead system in accordance with embodiments of the invention. FIG. 3 depicts yet another embodiment where the IMD 36 is implanted in the right chest. Right phrenic nerve 22 stimulation is obtained by a right brachiocephalic lead 58 with bipolar electrodes 91 in right brachiocephalic vein 24 or superior vena cava 34. The right brachiocephalic lead 58 may be stabilized by way of a fixation feature, for example a helix, in the right internal jugular vein 39. Respiratory sensing information may be obtained from one or more bipolar electrodes 91 in combination with IMD 36 housing. Alternatively or in combination, a separate multi-electrode or large electrode lead (not shown) in Azygos Vein 18 may be used for respiratory sensing in combination with one or more bipolar electrodes 91 or IMD 36 housing. Alternatively or in combination, electrodes 71 and 72 on cardiac pacing right atrial lead 70 or electrodes 63, 64, 65 on right ventricle lead 60 may be used for respiratory sensing in combination with one or more bipolar electrodes 91 or IMD 36 housing.

Figure 4:
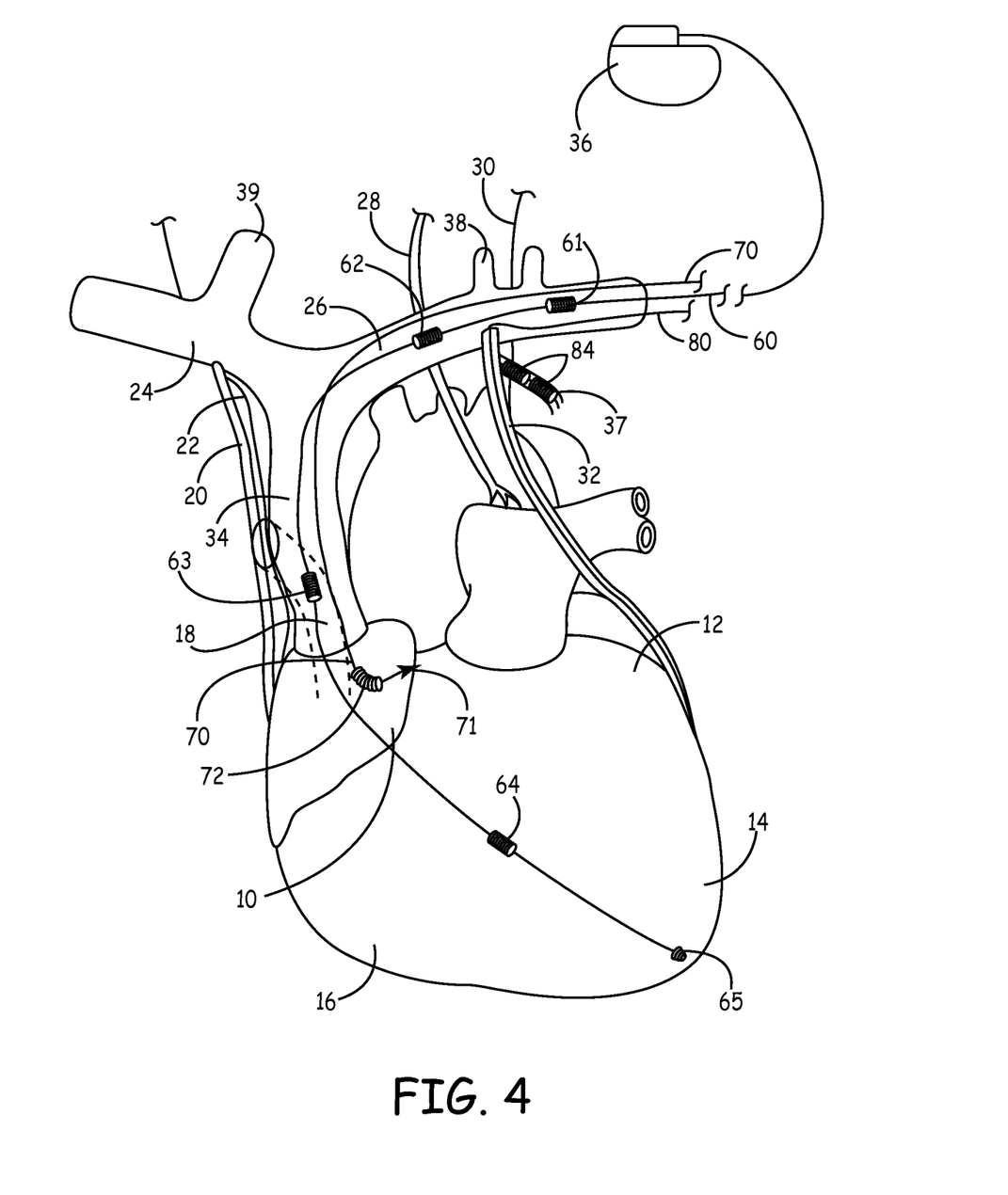
FIG. 4 is a schematic view of a device and lead system in accordance with embodiments of the invention.

FIG. 4 is a schematic view of a device and lead system in accordance with embodiments of the invention. FIG. 4 depicts another embodiment where the IMD 36 is implanted in the left chest. Left phrenic nerve 30 stimulation is obtained by bipolar electrodes 84 on left phrenic lead 80 placed in the left superior intercostal vein 37. One or more of the bipolar electrodes 84 or cardiac pacing electrodes on right atrial lead 70 or right ventricular lead 60 are used for sensing with IMD 36 housing used as second sensing electrode.

In yet another embodiment (not depicted) the IMD 36 could be implanted in either the right or left chest. Right and/or left pulmonary plexus stimulation is obtained by a lead implanted in the right and/or left pulmonary artery, the aforementioned lead having bipolar electrodes. The lead is stabilized by way of a fixation feature, for example a helix, in the pulmonary artery. Respiratory sensing information may be obtained from one or more bipolar electrodes on the lead in combination with IMD 36 housing. Alternatively or in combination, electrodes on a cardiac pacing right arterial lead or on a right ventricle lead may be used for respiratory sensing in combination with one or more bipolar electrodes on one or both of the pulmonary plexus leads, or IMD 36 housing.

Figure 5:
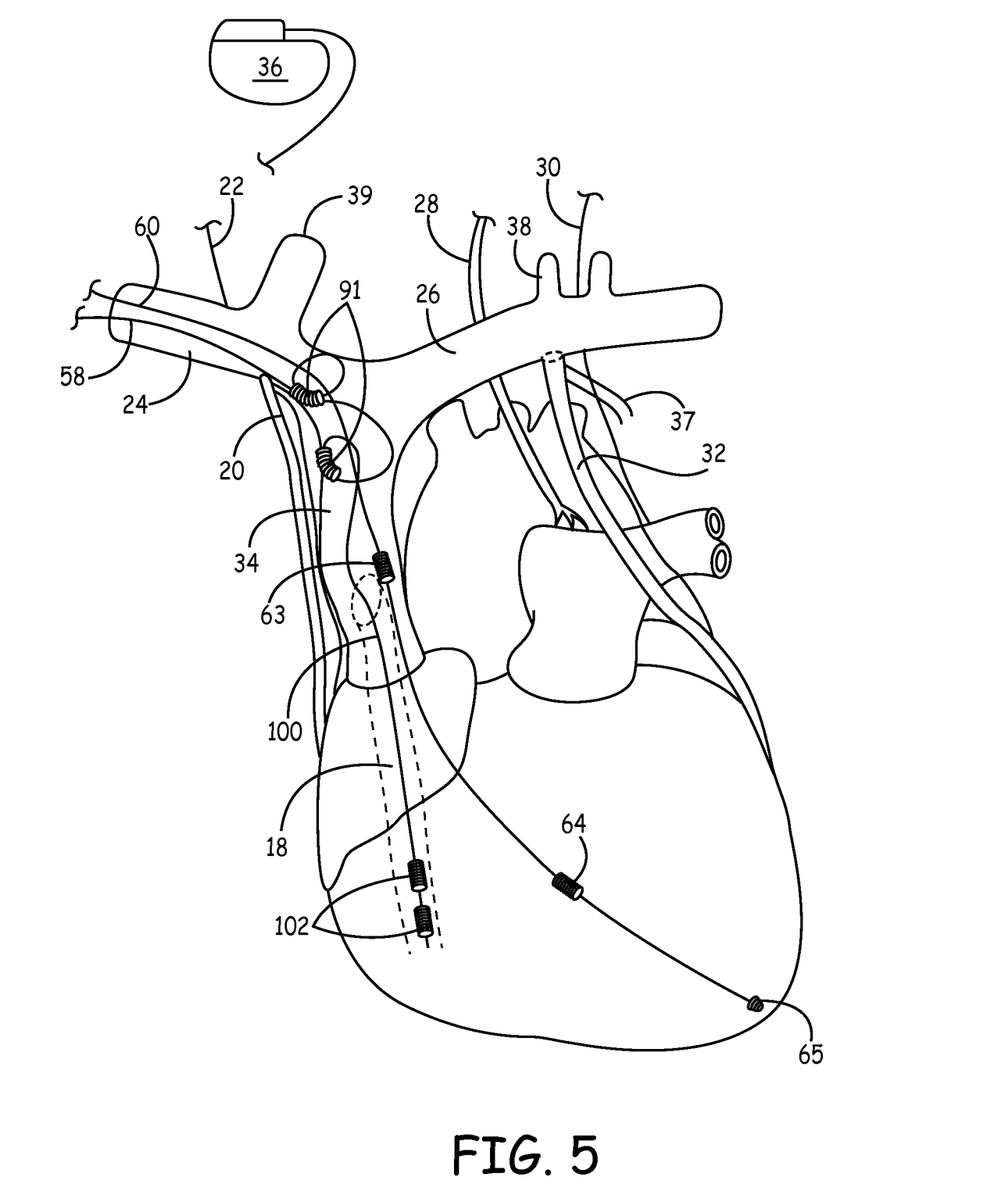
FIG. 5 is a schematic view of a device and lead system in accordance with embodiments of the invention.

FIG. 5 is a schematic view of a device and lead system in accordance with embodiments of the invention. The IMD 36 of FIG. 5 is implanted in the right chest. A right brachiocephalic lead 58 has at least one electrode 91 usable to stimulate the right phrenic nerve 22. The right brachiocephalic lead 58 of this embodiment has fixation biases that not only stabilize and retain the lead 58 within the vein 24, but also orient the electrode 91 in a position within the vein 58 so as to facilitate stimulation of the right phrenic nerve 22. Leads of this type are disclosed in U.S. patent application Ser. No. 12/330,095, which is hereby incorporated by reference.

The embodiment in FIG. 5 also includes a respiration sensing lead 100 situated in the azygos vein 18, the respiration lead 100 having at least one electrode 102 that cooperates with other electrodes on other leads or on the IMD 36 itself to monitor respiration by measuring impedance changes. In cases where the IMD 36 provides the sensing vector with the electrode 102, the vector will capture a cross section of the lung both cranial to caudal as well as anterior to posterior. In the embodiment of FIG. 5, the sensing lead 100 is integral with the right brachiocephalic lead 58. Where possible, integrating leads in this fashion to form a single pass lead that performs more than one function can simplify implantation of a device. In this instance, the single pass lead may be simpler to implement because the exact location of the electrode 102 in the azygos vein 18 is not crucial for the impedance measuring application.

The embodiment of FIG. 5 includes a right ventricular lead 60 with electrodes 63, 64, and 65. In some applications electrode 65 could be a combination of a tip electrode configured to secure itself to the heart muscle and a nearby ring electrode used for padding the heart. Electrodes 63 and 64 could be coil electrodes used in conjunction with and active housing of the IMD to provide defibrillation pulses if required.

Figure 6:
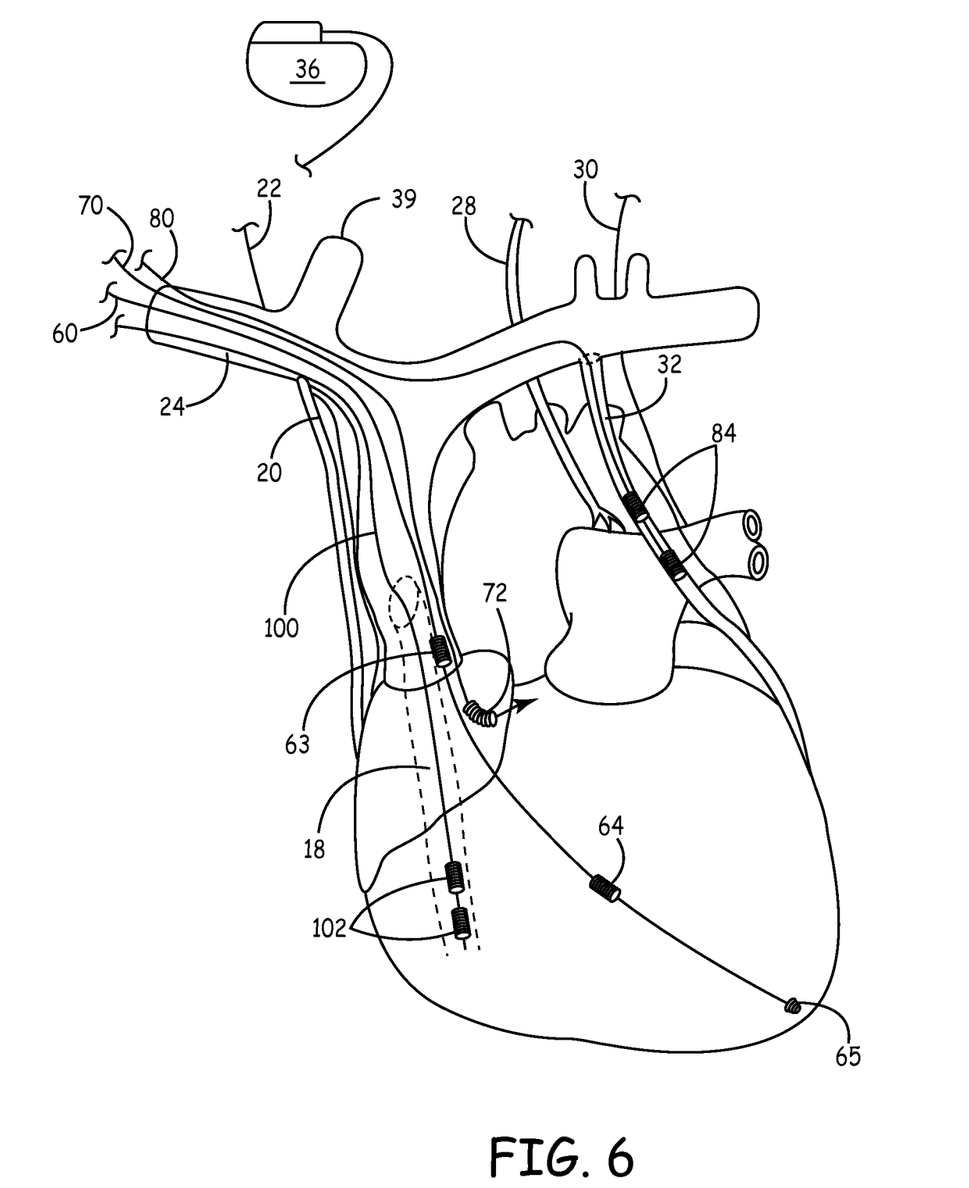
FIG. 6 is a schematic view of a device and lead system in accordance with embodiments of the invention.

FIG. 6 is a schematic view of a device and lead system in accordance with embodiments of the invention. The IMD 36 of FIG. 6 is implanted in the right chest. A left phrenic lead 80 is fed from the right brachiocephalic 24 across to the left pericardiophrenic vein 32. The left phrenic lead 80 has at least one electrode 84 usable to stimulate the left phrenic nerve 30 to modify breathing. A right atrial lead 70 has an electrode 72 for pacing the right atrium, and a right ventricular lead 60 has electrodes 63, 64, and 65 for pacing the right ventricle and/or defibrillation. A left ventricular lead (not shown) may also be employed for CRT therapy if indicated. A respiration sensing lead 100 is deployed in the azygos vein 18 and includes at least one electrode 102 that can be used to measure impedance changes across lung tissue to electrodes located on the IMD 36 or on other leads.

Figure 7:
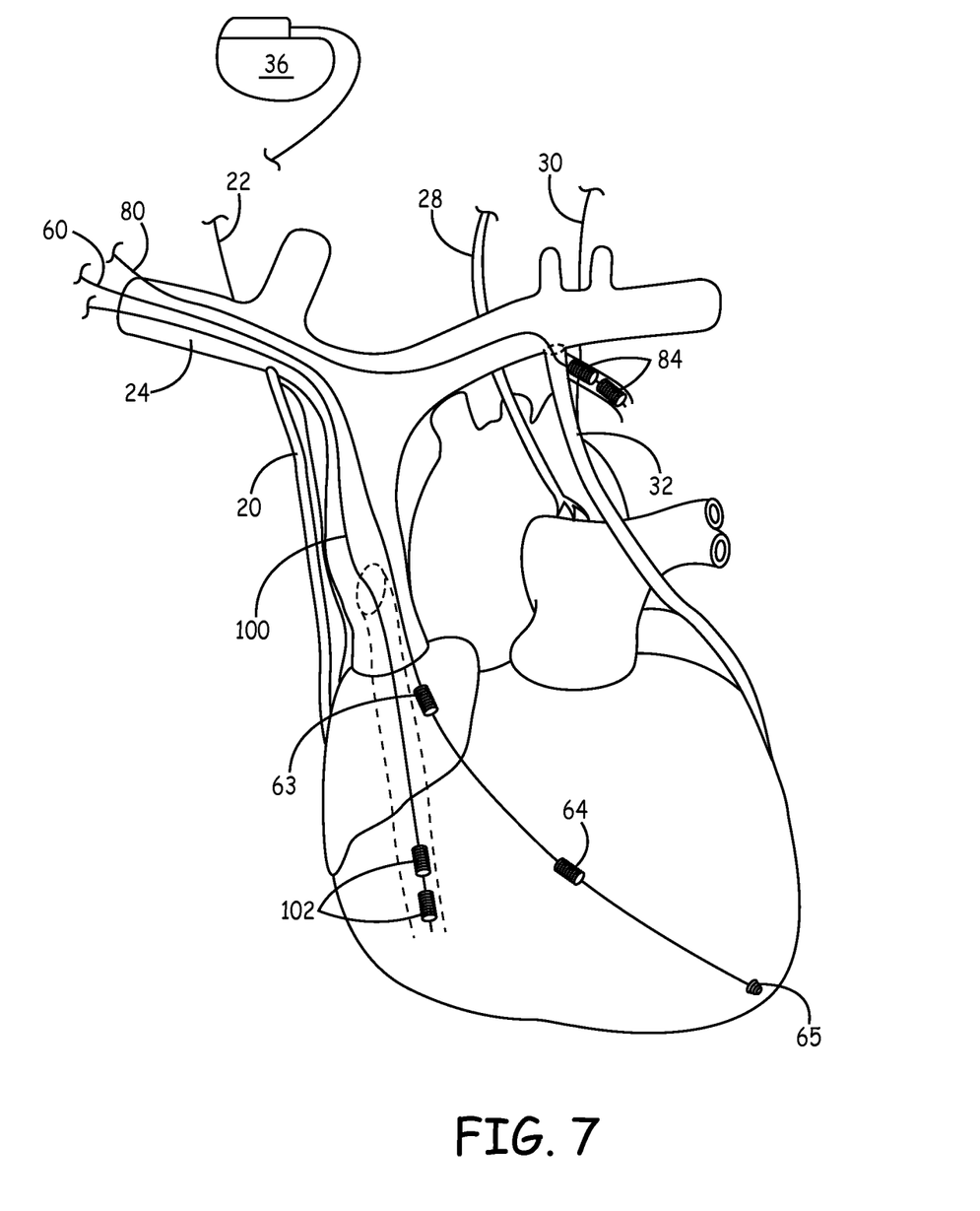
FIG. 7 is a schematic view of a device and lead system in accordance with embodiments of the invention.

FIG. 7 is a schematic view of a device and lead system in accordance with embodiments of the invention. The IMD 36 of FIG. 7 is implanted in the right chest. The embodiment of FIG. 7 includes a left phrenic lead 80 that is fed from the right brachiocephalic 24 across to a left superior intercostal vein 37. The left phrenic lead 80 has at least one electrode 84 usable to stimulate the left phrenic nerve 30 to modify breathing. A right ventricular lead 60 has electrodes 63, 64, and 65 for pacing the right ventricle and/or defibrillation. A left ventricular lead (not shown) may also be employed for CRT therapy if indicated. A respiration sensing lead 100 is deployed in the azygos vein 18 and includes at least one electrode 102 that can be used to measure impedance changes across lung tissue to electrodes located on the IMD 36 or on other leads.

Figure 8:
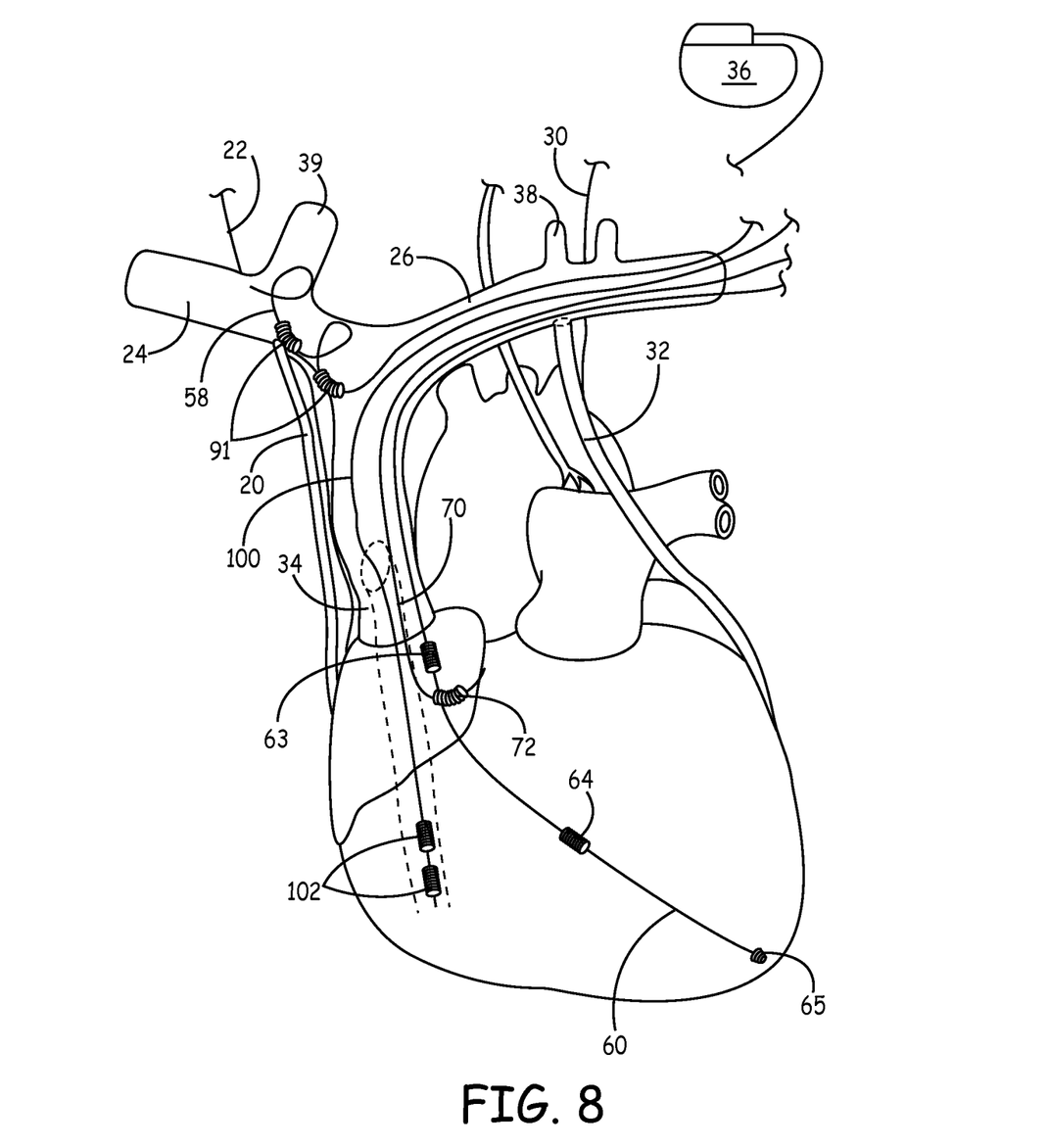
FIG. 8 is a schematic view of a device and lead system in accordance with embodiments of the invention.

FIG. 8 is a schematic view of a device and lead system in accordance with embodiments of the invention. The IMD 36 of FIG. 8 is implanted in the left chest. The embodiment of FIG. 8 includes a right brachiocephalic lead 58 that is fed from the left brachiocephalic vein 26 across to the right brachiocephalic vein 24. The right brachiocephalic lead 58 has at least one electrode 91 usable to stimulate the right phrenic nerve 22. The right brachiocephalic lead 58 of this embodiment has fixation biases that not only stabilize and retain the lead 58 within the vein 24, but also orient the electrode 91 in a position within the vein 58 so as to facilitate stimulation of the right phrenic nerve 22.

The embodiment of FIG. 8 also includes a right ventricular lead 60 with electrodes 63, 64, and 65 and a right atrial lead 70 with electrode 72. A left ventricular lead (not shown) may also be employed with this embodiment. A respiration sensing lead 100 is fed from the left brachiocephalic vein 26 to the superior vena cava 34 and into the azygos vein 18. The respiration sensing lead 100 located in the azygos 18 may also be configured to include a coil electrode or other electrode capable of providing high energy defibrillation pulses in cooperation with an electrode on the IMD 36 or elsewhere within the system. This electrode location may be useful for providing high energy cardiac therapy in patients where heat based electrodes are more difficult to employ, perhaps due to prior heart valve replacements or other issues.

Transthoracic impedance is used to chronically measure the respiratory effort of a patient within the constraints of an implantable system. Some embodiments in accordance with the invention employ a respiration sensing lead 100 located in the azygos vein 18. The azygos vein 18 is used in these embodiments for several reasons. The azygos vein is located generally toward the posterior of a patient and extends through the diaphragm so that electrodes can be located near or below the bottom of the lung. When the measurement vector is taken from this location to the IMD 36 in the front chest a large portion of the lung can be measured.

Another advantage of the azygos location is a reduced concern relating to nearby excitable tissue. This allows for the use of higher energy levels than may be acceptable in other possible locations for impedance measuring. Also the relatively central location allows for measurement using an IMD 36 implanted in either the left pectoral region or right pectoral region to measure either lung, and the measurement vectors capture very little of the heart reducing interference from blood flow and other factors. The azygos runs relatively parallel to the lungs, so the actual depth of the location of electrodes is less important. Inventors have noticed little patient to patient variability regarding azygos vein anatomy.

Figure 9:
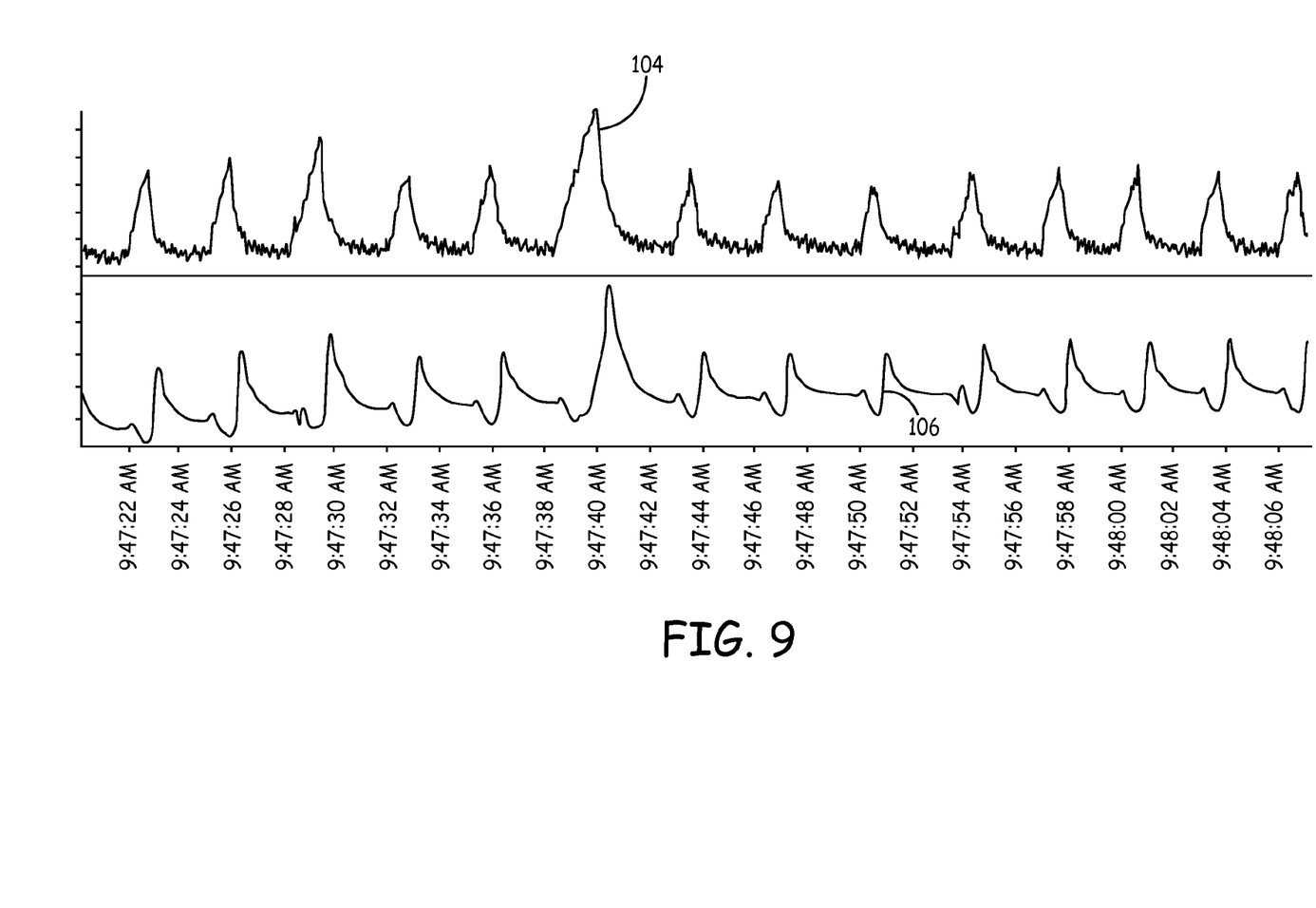
FIG. 9 is an experimental waveform of a transthoracic impedance measurement.

FIG. 9 is an experimental waveform of a transthoracic impedance measurement. The top waveform 104 is a signal from a lead placed in the azygos vein of a porcine subject measuring impedance to an electrode placed on the chest to emulate an IMD electrode. The bottom waveform 106 is a thoracic respiratory belt. The comparison shows the high quality signal possible in an implantable device.

Experimental data with a porcine model was performed by applying a current of 0.5 mA, measuring the resulting voltage, and calculating the impedance. This method was performed using both an azygos lead and a right atrial lead, with a IMD electrode emulator at both the right and left chest The difference between beginning of inspiration and peak of inspiration, essentially the measurement of breathing, was calculated. The difference when using an azygos lead was on the order of four to ten times greater than the measured difference using a right atrial lead (3-5 ohms from azygos, 0.5-1 ohms from right atrium). Experiments were also conducted in humans and the impedance change during respiration was on the order of 5 ohms, compared to a more typical 1-1.25 ohms seen in patients when measured from the right atrium to a left implant.

The azygos penetrates the diaphragm muscle, so it is possible to use this location to sense the diaphragmatic electromyography ("EMG") signal by locating electrodes near the diaphragm, and possibly locating one near the diaphragm position at exhalation and one near the diaphragm position at inhalation. This sensed signal would be much more difficult from a more traditional right ventricle lead placement and impossible for a right atrial lead placement.

Figure 10:
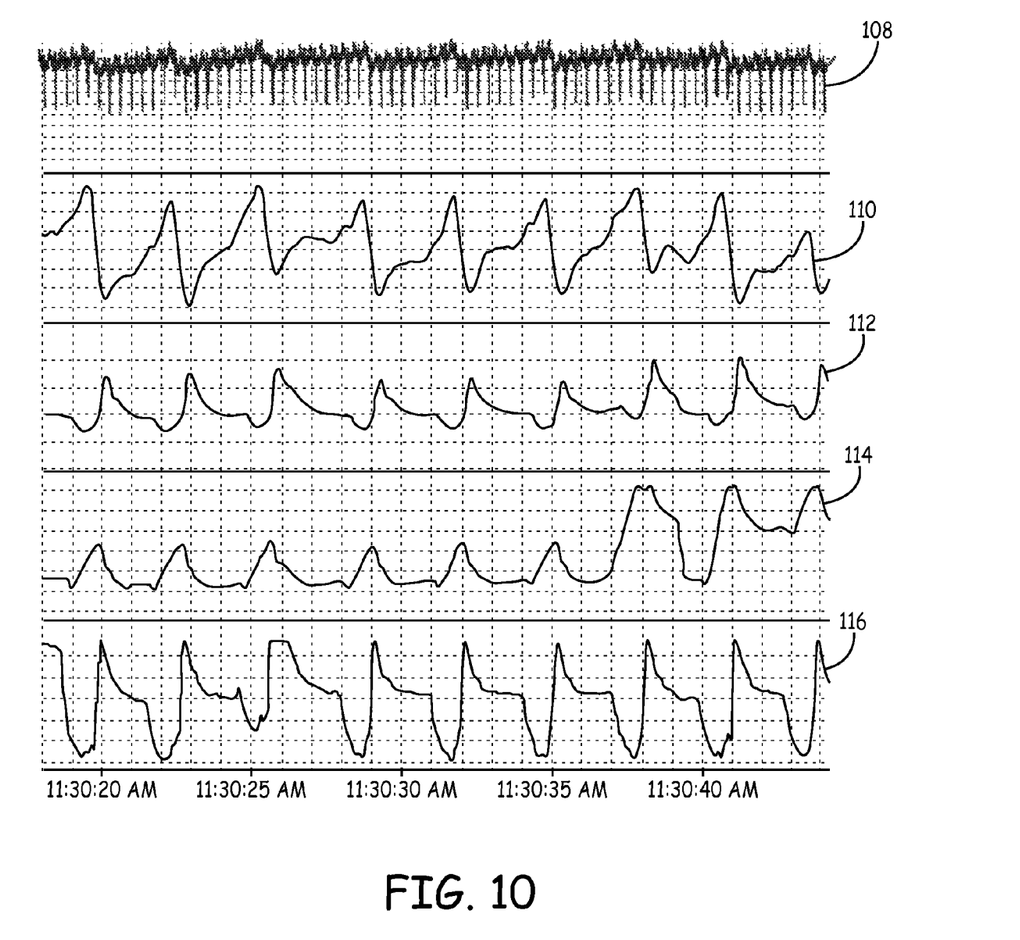
FIG. 10 is an experimental waveform of a diaphragmatic EMG measurement.

FIG. 10 is an experimental waveform of a diaphragmatic EMG measurement. The first waveform 108 is an unfiltered EMG signal from a porcine subject. The second waveform 110 is the filtered EMG signal representative of diaphragmatic muscle effort and, in an unobstructed airway, respiration. The third waveform 112 is a signal from a thoracic respiratory belt, and the fourth 114 is a signal from an abdominal belt. The fifth waveform 116 is an indication of nasal pressure.

Inventors believe that a single azygos lead capable of providing both transthoracic impedance and diaphragmatic EMG can discriminate between obstructive and central apneas. During an obstructive sleep apnea event, airflow is restricted, usually due to an upper airway collapse. In these cases there is diaphragmatic effort as the patient is still trying to breathe, but transthoracic impedance does not increase as in a normal breath because the impedance is not raised as much with reduced air in the lungs. An implantable device capable of distinguishing between obstructive sleep apnea, where breathing is reduced due to airway closure, and central sleep apnea, where a lack of respiratory drive results in reduced diaphragmatic effort, may be very useful in treating respiratory disorders.

The IMD shown in FIGS. 1-8 and described elsewhere may be coupled to several lead systems. In some embodiments there may be a first lead system associated with cardiac defibrillation, a second lead system associated with cardiac pacing or CRT, a third lead system associated with respiration sensing, and/or a fourth lead system associated with phrenic nerve stimulation for respiration modulation and control.

In some embodiments the IMD contains sense amplifier circuitry coupled to electrodes within the various lead systems to detect the EMG of the heart from a variety of locations. Conventional pacing and defibrillation algorithms are used to determine whether or not the observed cardiac rhythm is normal or abnormal and to provide an appropriate therapy to the heart. Pacing therapies are delivered through output pulse generators contained within the IMD and coupled to electrodes in the lead systems for delivering low voltage, low current stimuli which caused the heart to contract. Some pacing therapies deliver stimuli that do not provoke contraction but rather extend refractory periods of cardiac tissues to promote control of arrhythmia.

Higher voltage and higher current output circuits are available in the IMD to provide cardioversion therapy or defibrillation therapy to the heart in response to detected arrhythmias such as ventricular fibrillation or ventricular tachycardia. Coil electrodes present within the left or right heart, the azygos vein, or elsewhere may steer and direct current through a large portion of the cardiac tissue to promote defibrillation.

The availability of a large number of electrode sites throughout the chest cavity and heart permits selection of various electrodes for particular electronic functions. For example, a multiplexer under control of logic within the IMD can tie together various electrodes to serve as reference or ground for sensing activities on other electrodes. In a similar fashion the availability of knowledge of the respiratory cycle and cardiac cycle permits the timing or delivery of therapies at optimal times. For example, it may be preferable to delivery defibrillation energies at a time when respiration monitoring indicates minimum lung volume to help steer current through the heart with lower impedance. As an additional example, historic knowledge of lung impedance and cardiac impedance may be a useful diagnostic monitor for the progression of congestive heart failure or other disease processes. The multiplexer permits the individual selection or the exclusion of certain electrodes pairs to optimize sensing or overcome deficiencies in sensing.

At this time it is widely known in the industry how to implement cardiac defibrillation, cardiac pacemaking and cardiac resynchronization therapy ("CRT") or biventricular pacing systems so detailed description of their structures and functionalities are not required to carry out the present invention. There are also many well known therapies using phrenic nerve stimulation to treat respiratory deficiencies, as well as emerging technologies. One exemplary application is the treatment of disordered breathing conditions such as central sleep apnea, which often accompanies heart failure making a combination device as disclosed herein particularly relevant.

Applicants hereby incorporate the disclosures of pending U.S. patent applications Ser. Nos. 12/163,500 and 11/601,150, which disclose therapies that may be implemented using transvenous phrenic nerve stimulation. When the phrenic nerve is stimulated in accordance with some of these embodiments, it may be advantageous to correlate the duration of the phrenic nerve stimulation signal to the heart rate. For example, as the heart rate increases the duration of the phrenic nerve stimulation signal may be reduced so as to allow breathing rate to more naturally adjust to increased heart rate.

Devices in accordance with embodiments of the invention may detect and treat cardiac arrhythmias such as ventricular fibrillation and ventricular tachycardia. In these embodiments an implantable device detects the initiation of arrhythmias and terminates them by delivery of one or more high voltage electrical impulses to the heart. The energy of these impulses is large compared to the energy of impulses delivered by an artificial pacemaker, which is used to pace the heart but not to terminate fibrillation and arrhythmias. This feature may lead to patients experiencing uncomfortable electrical discharges of the IMD. Also, battery life is affected significantly by the higher energy of these discharges. High energy IMD discharges can also damage the heart tissue itself and may make the heart more susceptible to future arrhythmias.

Respiration and lung inflation may alter thoracic impedance and have an effect on the efficiency of energy delivery to the heart by IMDs designed to treat arrhythmias. Phrenic nerve stimulation in accordance with embodiments of the invention can controllably alter respiration and therefore influence the conditions that determine efficiency of defibrillation and cardioversion. Devices or and methods in accordance with embodiments of the invention may optimize defibrillation using transvenous stimulation of a phrenic nerve.

In one embodiment in accordance with the invention, respiration sensing performed by the IMD allows the high energy cardac shock to be timed with any portion of the respiration cycle found to be desirable, for example at the end of expiration. If phrenic nerve stimulation is being applied therapeutically, stimulation of the phrenic nerve can be stopped at the time of the high energy cardiac pulse to allow timely exhalation and avoid the condition of high thoracic impedance that may be created by stimulation.

Many IMDs used to provide high energy pulses for cardiac therapy require a few seconds or more to charge a capacitor or other energy storage device after a cardiac event is detected. In one embodiment in accordance with the invention, phrenic nerve stimulation may be used to hyperventilate the patient by stimulating to provide for several rapid and/or deep breaths while the IMD is charging or preparing to deliver a therapeutic pulse. When the IMD is ready to deliver the pulse or signal, phrenic nerve stimulation is stopped. A period of apnea or reduced breathing follows the induced hyperventilation. The high energy cardiac pulse may be delivered during the apnea or reduced breathing period to increase pulse efficiency. In some embodiments, the last breath before the cardiac pulse is given may be held for a short time and then released so that the cardiac pulse may be timed to coincide with the end of expiration or any other desired period in the breathing cycle.

After the cardiac pulse is delivered and confirmed to be efective another period of rapid deep breathing can optionally be created to improve perfusion of the heart and oxygenation of blood.

In addition, the ability of integrated phrenic stimulation to still the lungs by either generating deep inspiration and holding the breath or by hyperventilating the patient to induce temporary apnea can be useful for the diagnostic function of the IMD. It is known that respiration interferes with electrocardiogram ("ECG") monitoring. If a critical desision needs to be made by the ICD logic to discriminate between various types of arrhythmias, supressing respiratory motion for a short period of time can be helpful by reducing noise and improving analysis.

One skilled in the art will appreciate that the invention can be practiced with embodiments other than those disclosed. The disclosed embodiments are presented for purposes of illustration and not limitation, and the invention is limited only by the claims that follow.

What is claimed is:

1. An implantable medical device comprising:
   a. an intravascularly implantable cardiac lead configured for stimulating cardiac tissue;
   b. an intravascularly implantable respiration lead configured for transvascularly stimulating a phrenic nerve;
   c. an intravascularly implantable intercostal lead with at least one electrode configured to be located in an intercostal vein;
   d. an implantable medical device with at least one external electrode configured to be implanted subcutaneously in a patient's chest;
   e. circuitry within the implantable medical device configured to measure impedance between the at least one electrode on the intercostal lead when the electrode is located in an intercostal vein of a patient and the at least one electrode on the implantable medical device when the device implanted subcutaneously in the patient; and
   f. circuitry within the implantable medical device configured to stimulate the phrenic nerve using the stimulation electrode.

2. The lead system of claim 1, wherein:
   a. the cardiac lead is selected from a group consisting of a pacemaker lead, a defibrillation leads, and a CRT lead; and
   b. the respiration lead is installed in a pericardiophrenic vein.

3. The lead system of claim 1, wherein:
   a. the cardiac lead is selected from a group consisting of a pacemaker lead, a defibrillation lead, and a CRT lead; and
   b. the respiration lead is installed in a brachiocephalic vein.

4. The lead system of claim 3, wherein the respiration lead has pre-formed biases that assist in stabilizing the lead in the vein and positioning electrodes on the lead proximate a phrenic nerve.

5. The lead system of claim 1, wherein:
   a. cardiac lead is selected from a group consisting of a pacemaker lead, a defibrillation leads, and a CRT lead; and
   b. the respiration lead is installed in an internal jugular vein.

6. The lead system of claim 5, wherein the respiration lead has pre-formed biases that assist in stabilizing the lead in the vein and positioning electrodes on the lead proximate a phrenic nerve.

7. The lead system of claim 1, wherein:
   a. the cardiac lead is selected from a group consisting of a pacemaker lead, a defibrillation lead, and a CRT lead; and
   b. the respiration lead is installed in a superior intercostal vein.

8. A respiration sensing and stimulation system for use with an implantable medical device comprising:
   a. an intravascular intercostal lead with at least one electrode configured to be located in an intercostal vein;

b. an implantable medical device with at least one electrode configured to be implanted subcutaneously in a patient's chest;
c. circuitry within the implantable medical device configured to measure impedance between the at least one electrode on the intercostal lead when the electrode is located in an intercostal vein of a patient and the at least one electrode on the implantable medical device when the device implanted subcutaneously in the patient;
d. at least one stimulation electrode that is configured to be positioned proximate a phrenic nerve; and
e. circuitry within the implantable medical device configured to stimulate the phrenic nerve using the stimulation electrode.

9. The respiration sensing system of claim 8, wherein the intercostal vein is a superior intercostal vein.

10. The respiration sensing system of claim 8, wherein at least one electrode on the intercostal lead is configured to be located proximate a diaphragm and the circuitry is configured to sample impedance measurements between the at least one electrode on the intercostal lead when the electrode is located in an intercostal vein of the patient and the at least one electrode on the implantable medical device when the device is implanted subcutaneously in the patient at a first interval and the circuitry is further configured to sample diaphragmatic EMG at the electrode proximate the diaphragm when the electrode is located in an intercostal vein of the patient at a second or offset interval so that samples of impedance and EMG can be taken at separate times.

11. The respiration sensing system of claim 8, wherein at least one electrode on the intercostal lead is configured to be located proximate a diaphragm and the circuitry is configured to sample impedance measurements between the at least one electrode on the intercostal lead when the electrode is located in an intercostal vein of the patient and the at least one electrode on the implantable medical device when the device is implanted subcutaneously in the patient at a first interval and the circuitry is further configured to sample electrocardiogram measurements between the at least one electrode on the intercostal lead when the electrode is located in an intercostal vein of the patient and the at least one electrode on the implantable medical device when the device is implanted subcutaneously in the patient at a second or offset interval so that samples of impedance and electrocardiogram measurements can be taken at separate times.

12. The respiration sensing system of claim 8, wherein at least one electrode on the intercostal lead is configured to be located proximate a diaphragm and the circuitry is configured to sample impedance measurements between the at least one electrode on the intercostal lead when the electrode is located in an intercostal vein of the patient and the at least one electrode on the implantable medical device when the device is implanted subcutaneously in the patient at a first interval and is configured to sample diaphragmatic EMG at an electrode proximate the diaphragm at a second interval and is configured to sample electrocardiogram measurements between the at least one electrode on the intercostal lead when the electrode is located in an intercostal vein of the patient and the at least one electrode on the implantable medical device when the device is implanted subcutaneously in the patient at a third interval so that samples of each of the three measurements can be taken at separate times.

13. A sensing and stimulation system comprising:
a. an intravascular intercostal lead with at least two electrodes configured to be located in an intercostal vein proximate a diaphragm;
b. circuitry that is configured to sample measurements of diaphragmatic EMG based on signals received by the at least two electrodes when the electrodes are located in an intercostal vein of a patient;
c. at least one stimulation electrode that is configured to be positioned proximate a phrenic nerve on the same intercostal lead as the other electrodes; and
d. circuitry within the implantable medical device configured to stimulate the phrenic nerve using the stimulation electrode.

14. The sensing system of claim 13, further comprising an implantable medical device having at least one electrode configured to be implanted subcutaneously in a patient's chest and circuitry that is configured to sample electrocardiogram measurements between at least one electrode on the intercostal lead when the electrode on the intercostal lead is located in an intercostal vein of the patient and the at least one electrode on the implantable medical device at an interval so that samples of diaphragmatic EMG and electrocardiogram signals can be taken at separate times.

15. A method of modifying and detecting respiration by stimulating a phrenic nerve and sensing impedance between an electrode located on a lead and disposed in an intercostal vein of a patient and a second electrode located elsewhere in the patient.

16. The method of claim 15, wherein the second electrode is located on an implantable medical device that contains circuitry configure to sense the impedance between the electrodes and stimulate the phrenic nerve.

17. The method of claim 15, wherein the second electrode is located on a second lead implanted in a brachiocephalic vein.

* * * * *